United States Patent [19]

Schroeder et al.

[11] Patent Number: 5,426,235
[45] Date of Patent: Jun. 20, 1995

[54] PREPARATION OF CYCLIC KETONES

[75] Inventors: Juergen Schroeder; Klaus Ebel; Charles Schommer, all of Ludwigshafen, Germany

[73] Assignee: BASF Aktiengesellschaft, Ludwigshafen, Germany

[21] Appl. No.: 251,041

[22] Filed: Jun. 1, 1994

[30] Foreign Application Priority Data

Jun. 30, 1993 [DE] Germany ............... 43 21 692.7

[51] Int. Cl.$^6$ ............................................. C07C 45/48
[52] U.S. Cl. ...................................... 568/338; 568/355
[58] Field of Search ................ 508/355, 338; 562/590

[56] References Cited

U.S. PATENT DOCUMENTS

| | | | |
|---|---|---|---|
| 3,142,696 | 7/1964 | Mihara et al. | 568/355 |
| 3,454,619 | 7/1969 | Hayes | 568/355 |
| 3,492,345 | 1/1970 | Neugebauer et al. | 562/590 |
| 4,745,228 | 5/1988 | Decker et al. | 568/355 |
| 4,788,343 | 11/1988 | Kleine-Homann et al. | 568/355 |
| 4,822,920 | 8/1989 | Lermer et al. | 568/355 |
| 4,895,985 | 1/1990 | Decker et al. | 568/355 |

FOREIGN PATENT DOCUMENTS

| | | |
|---|---|---|
| 251111 | 1/1988 | European Pat. Off. . |
| 415259 | 8/1934 | United Kingdom ............... 568/338 |

*Primary Examiner*—James H. Reamer
*Attorney, Agent, or Firm*—John H. Shurtleff

[57] ABSTRACT

Cyclic ketones of the general formula I

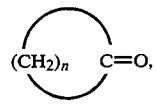 (I)

where n is an integer from 4 to 6, are prepared by reacting aliphatic dicarbonitriles of the general formula II $$NC-(CH_2)_n-CN \qquad (II),$$

where n has the abovementioned meaning, in the gas phase in the presence of water at from 250° to 500° C. on solid oxide catalysts.

10 Claims, No Drawings

PREPARATION OF CYCLIC KETONES

The present invention relates to a process for preparing cyclic ketones by reaction of aliphatic dicarbonitriles at elevated temperature on solid oxide catalysts.

EP-A 251 111 discloses a process for preparing cyclic ketones from aliphatic dicarboxylic esters on oxide catalysts at from 300° to 345° C. Only moderate yields are obtained in the preparation of cycloheptanone. The process is also susceptible to improvements in that the dicarboxylic esters need first to be prepared from the more readily available dicarboxylic acids or dicarbonitriles.

It is an object of the present invention to remedy the abovementioned disadvantages.

We have found that this object is achieved by a novel and improved process for preparing cyclic ketones of the general formula I

$(CH_2)_n \quad C=O,$ (I)

where n is an integer from 4 to 6, which comprises reacting aliphatic dicarbonitriles of the general formula II

$NC-(CH_2)_n-CN$ (II), where n has the abovementioned meaning, in the gas phase in the presence of water at from 250° to 500° C. on solid oxide catalysts.

The process according to the invention can be carried out as follows:

A mixture of dicarbonitrile II and water can be passed, preferably in the gas phase, over the catalyst which has been heated to the reaction temperature of from 250° to 500° C., preferably 300° to 400° C. The reaction pressure may be varied within wide limits and is, as a rule, from 0.01 to 50 bar, preferably 0.1 to 5 bar, particularly preferably atmospheric pressure. It is also possible where appropriate to introduce gases which are inert under the reaction conditions, such as nitrogen or argon. The gas mixture leaving the reactor can be condensed, and the organic phase can be separated off and fractionally distilled.

Suitable as starting compound II are adiponitrile, pimelonitrile and suberonitrile.

Suitable and preferred solid oxide catalysts are elements of groups oxides of the inorganic IIIa and/or IVa and/or IVb of the periodic table of the elements and/or of zinc, such as boron oxide, aluminum oxide, gallium oxide, silicon dioxide, germanium dioxide, tin dioxide, titanium dioxide, zirconium dioxide, hafnium dioxide and zinc oxide, preferably aluminum oxide, silicon dioxide, zinc oxide and titanium dioxide and mixtures thereof. Very particularly suitable are mixtures of aluminum oxide or silicon dioxide and titanium dioxide.

Although it is possible to carry out the reaction according to the invention with the addition of stoichiometric amounts of water, a remarkable increase in the selectivity and useful life are achieved with an at least 3-fold stoichiometric excess of water. As a rule, the molar ratio of water to dicarbonitrile II is from 3:1 to 200:1, preferably 4:1 to 50:1, particularly preferably 5:1 to 30:1.

The reaction can be carried out batchwise or continuously in a fixed bed reactor, in a liquid-phase or trickle process, or in a fluidized bed reactor.

Compared with known processes, the process according to the invention provides cyclic ketones in a more straightforward and economic way.

The cyclic ketones obtainable by the process according to the invention are valuable intermediates for synthesizing crop protection agents and pharmaceuticals.

EXAMPLES

Example 1

40.8 g of suberonitrile and 97.2 g of water are vaporized each hour and passed with 90 l (STP)/h nitrogen through a fluidized bed reactor at 360° C. The fluidized bed reactor is packed with 500 ml of a catalyst composed of 75% by weight of titanium dioxide and 25% by weight of gamma-aluminum oxide. The reaction gases are subsequently condensed and the phases are separated. 28.5 g of cycloheptanone are obtained each hour (85% of theory based on suberonitrile).

Example 2

36.6 g of pimelonitrile and 97.2 g of water are vaporized each hour and passed with 90 l(STP)/h nitrogen through a fluidized bed reactor at 360° C. The fluidized bed reactor is packed with 500 ml of a catalyst composed of 75% by weight of titanium dioxide and 25% by weight of gamma-aluminum oxide. The reaction gases are subsequently condensed and the phases are separated. 7.9 g of cyclohexanone are obtained each hour (27% of theory based on pimelonitrile).

Example 3

32.4 g of adiponitrile and 97.2 g of water are vaporized each hour and passed with 90 i(STP)/h nitrogen through a fluidized bed reactor at 300° C. The fluidized bed reactor is packed with 500 ml of a catalyst composed of 75% by weight of titanium dioxide and 25% by weight of gamma-aluminum oxide. The reaction gases are subsequently condensed and the phases are separated. 18.1 g of cyclopentanone are obtained each hour (72% of theory based on adiponitrile).

Example 4

32.4 g of adiponitrile and 97.2 g of water are vaporized each hour and passed with 90 l(STP)/h nitrogen through a fluidized bed reactor at 300° C. The fluidized bed reactor is packed with 500 ml of a catalyst composed of 75% by weight of titanium dioxide and 25% by weight of silicon dioxide. The reaction gases are subsequently condensed and the phases are separated. 11.6 g of cyclopentanone are obtained each hour (46% of theory based on adiponitrile).

Example 5

40.8 g of suberonitrile and 64.8 g of water are vaporized each hour and passed with 170 l(STP)/h nitrogen through a fluidized bed reactor at 360° C. The fluidized bed reactor is packed with 500 ml of a catalyst composed of 75% by weight of titanium dioxide and 25% by weight of gamma-aluminum oxide. The reaction gases are subsequently condensed and the phases are separated. 25.1 g of cycloheptanone are obtained each hour (75% of theory based on suberonitrile).

We claim:
1. A process for preparing cyclic ketones of the formula

$$(CH_2)_n \quad C=O, \qquad I$$

where n is an integer from 4 to 6, which comprises:
reacting an aliphatic dicarbonitrile of the formula $$NC-(CH_2)_n-CN \qquad II,$$

where n has the abovementioned meaning, in the gas phase with a stoichiometric excess of water at from 250° to 500° C. and on a solid oxide catalyst selected from the group consisting of the inorganic oxides of elements of groups IIIa, IVa and IVb of the periodic table of elements, zinc oxide and mixtures thereof.

2. A process for preparing cyclic ketones I as claimed in claim 1, wherein aluminum oxide, silicon dioxide, zinc oxide and/or titanium dioxide are employed as solid oxide catalysts.

3. A process for preparing cyclic ketones I as claimed in claim 1, wherein the reaction is carried out at from 300° to 400° C.

4. A process for preparing cyclic ketones I as claimed in claim 1, wherein water and the aliphatic dicarbonitriles II are employed in the molar ratio of from 3:1 to 200:1.

5. A process for preparing cyclic ketones I as claimed in claim 1, wherein water and the aliphatic dicarbonitriles II are employed in the molar ratio of from 4:1 to 50:1.

6. A process for preparing cyclic ketones I as claimed in claim 1, wherein water and the aliphatic dicarbonitriles II are employed in the molar ratio of from 5:1 to 30:1.

7. A process as claimed in claim 1, wherein water is employed in a stoichiometric excess of at least about 3:1, expressed as the molar ratio of water to the dicarbonitrile II.

8. A process as claimed in claim 1, wherein the solid oxide catalyst is a mixture of titanium dioxide and aluminum oxide.

9. A process as claimed in claim 1, wherein the solid oxide catalyst is a mixture of titanium dioxide and silicon dioxide.

10. A process as claimed in claim 1, wherein the reaction is carried out at from 300° to 400° C., a molar ratio of water to said dicarbonitrile of from 5:1 to 30:1, and on a solid oxide catalyst selected from the group consisting of aluminum oxide, silicon dioxide, zinc oxide, titanium oxide and mixtures thereof.

* * * * *

UNITED STATES PATENT AND TRADEMARK OFFICE
CERTIFICATE OF CORRECTION

PATENT NO. : 5,426,235
DATED : June 20, 1995
INVENTOR(S) : Schroeder et al.

It is certified that error appears in the above-identified patent and that said Letters Patent is hereby corrected as shown below:

COLUMN 3:

Claim 1, the formula I should read:

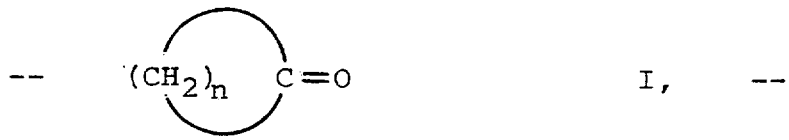

Signed and Sealed this

Fifth Day of September, 1995

Attest:

Attesting Officer

BRUCE LEHMAN

Commissioner of Patents and Trademarks